United States Patent
Thorner et al.

(10) Patent No.: US 7,078,514 B1
(45) Date of Patent: Jul. 18, 2006

(54) CHICKEN GROWTH HORMONE RELEASING HORMONE RECEPTOR

(75) Inventors: Michael O. Thorner, 3140 Plank Rd., North Garden, VA (US) 22959; Bruce David Gaylinn, 16172 Louisa Rd., Louisa, VA (US) 23093; Andrew Alan Toogood, Solihull (GB); Steve Harvey, 612 Hunters Close, Edmonton, Alberta (CA) T6R 2N2

(73) Assignees: Michael O. Thorner, N. Garden, VA (US); Bruce David Gaylinn, Louisa, VA (US); Andrew A. Toogood, West Midlands (GB); Steve Harvey, Alberta (CA)

( * ) Notice: Subject to any disclaimer, the term of this patent is extended or adjusted under 35 U.S.C. 154(b) by 680 days.

(21) Appl. No.: 10/009,643

(22) PCT Filed: Jun. 12, 2000

(86) PCT No.: PCT/US00/16135

§ 371 (c)(1),
(2), (4) Date: Dec. 12, 2001

(87) PCT Pub. No.: WO00/76455

PCT Pub. Date: Dec. 21, 2000

Related U.S. Application Data

(60) Provisional application No. 60/138,768, filed on Jun. 12, 1999, provisional application No. 60/176,387, filed on Jan. 14, 2000.

(51) Int. Cl.
*C07K 14/72* (2006.01)
(52) U.S. Cl. .................... 536/23.5; 530/350; 530/399
(58) Field of Classification Search ................ 530/350, 530/399, 300, 23.5; 424/185.1
See application file for complete search history.

(56) References Cited

U.S. PATENT DOCUMENTS 5,973,114 A * 10/1999 Thorner et al. ............ 530/350

FOREIGN PATENT DOCUMENTS

WO    WO 9832857 A1 *  7/1998

OTHER PUBLICATIONS

Porter et al., Ontogeny of growth hormone (GH)-secreting cells during chickent embryonic development: initial somatotrophs are responsive to GH-releasing hormone, Endocrinol. 136(5):1850-1856, 1995.*

Hiroyuki Kaiya et al., "Chicken Ghrelin: Purification, cDNA Cloning, and Biological Activity," *Endocrinology* 143(9):3454-3463 (2002) The Endocrine Society, Great Britain.

E.R. Kuhn et al., "The Release of Growth Hormone (GH): Relation to the Thyrotropic- and Corticotropic Axis in the Chicken," *Domestic Animal Endocrinology*, 29:43-51 (2005), Elsevier.

K. Peeters et al., "Effects of Pituitary Adenylate Cyclase-Activating Polypeptide (PACAP) on cAMP Formation and Growth Hormone Release from Chicken Anterior Pituitary Cells," *Annals New York Academy of Sciences*, 865:471-4 (1998).

M. Montero et al., "Molecular Evolution of the Growth Hormone-Releasing Hormone/Pituitary Adenylate Cyclase-Activating Polypeptide Gene Family. Functional Implication in the Regulation of Growth Hormone Secretion," *Journal of Molecular Endocrinology* 25:157-168 (2000), Society for Endocrinology, Great Britain.

S. Harvey, "Growth Hormone Secretion in Poikilotherms and Homeotherms," *The Endocrinology of Growth, Development, and Metabolism in Vertebrates* pp. 151-182. Eds PKT Pang, M Schriebman & CG Scanes (1993) Academic Press, New York.

A. O.L. Wong et al., Pituitary Adenylate Cyclase Activating Polypeptides as a Novel Hypophysiotropic Factor in Fish, *Biochemistry and Cell Biology* 78(3):329-343 (2000), NRC Research Press, Canada.

* cited by examiner

Primary Examiner—Brenda Brumback
Assistant Examiner—Claire M. Kaufman
(74) Attorney, Agent, or Firm—Buchanan Ingersoll PC

(57) ABSTRACT

The present invention relates to chicken growth hormone releasing hormone (GHRH), its corresponding receptor, and nucleic acid sequences encoding these proteins. More particularly the present invention is directed to the use of the chicken GHRH hormone and its corresponding GHRH receptor to enhance the production of larger, leaner chickens and other avian species used for meat production.

1 Claim, 3 Drawing Sheets

CHICKEN GROWTH HORMONE RELEASING HORMONE RECEPTOR

This application claims the benefit of 60/138/766 filed Jun. 12, 1999 and 60/176,387 filed Jan. 14, 2000.

FIELD OF THE INVENTION

The present invention is directed to chicken growth hormone releasing hormone GHRH receptor, ligands that bind to the GHRH receptor, and nucleic acid sequences encoding the GHRH receptor.

BACKGROUND OF THE INVENTION

Growth hormone releasing hormone (GHRH) is a hypothalamic hormone that acts at a pituitary receptor to stimulate the pulsatile release of GH. In mammals, GH is required for normal growth and development in the young, and has continuing importance in adults affecting such diverse functions as muscle maintenance, fat deposition, skin thickness, wound healing and exercise performance. GHRH also has direct effects on sleep. These actions have widespread clinical implications not only when considering GH deficiency syndromes, but also the sharply diminished GH levels that occur with aging and obesity. The anabolic and anticatabolic activities of GH have also recently been shown to ameliorate the muscle wasting and weight loss seen with AIDS.

GHRH and other regulators of the GH axis also have great potential in agricultural applications because they can stimulate growth and improve the efficiency of feed utilization. They control the relative partitioning of nutrients between muscle and fat and so may allow the production of leaner livestock and higher yields of milk, hair and feathers.

In birds, the function and regulation of GH are not well understood and thyroid releasing hormone (TRH) as well as gonadotropin releasing hormone (GnRH) appear to be a major factors in GH release. Research studies have been inconclusive as to the physiological role of GHRH in birds. A putative chicken GHRH polypeptide has been cloned and synthesized but found to have little or no GH releasing activity at chicken pituitary cells or in live chickens. Despite this, chicken pituitaries and live chickens do respond to mammalian GHRH with GH release. Studies in chickens using mammalian GHRH have not been successful in improving growth. Thus, it has been speculated that chickens have no functional GHRH receptor.

Furthermore, Southern blot analysis, using a human GHRH receptor probe and genomic DNA from human, monkey, rat, mouse, dog, cow, rabbit, chicken and yeast, detected GHRH receptors in all mammals tested, but not in chicken or yeast. These results indicate that GHRH receptors are well conserved in all the mammals tested, but absent or less well conserved in the chicken. Binding of human GHRH to chicken pituitary membranes suggests a high affinity G protein coupled receptor for GHRH is present in chicken. A similar experiment using the putative chicken GHRH and chicken pituitary membranes detected no specific binding. Thus the function of GHRH in birds is not understood and this prevents the development of its agricultural applications.

Further investigation of GHRH's role in avian development required the isolation of the corresponding GHRH receptor (GHRH-R). Purification of pituitary receptors is very difficult because of the scarcity of tissue, problems involving the solubilization of the receptors in active form, and in developing an efficient purification method. Therefore a need exists for the isolation of the gene that encodes the GHRH-R (or biologically active fragments thereof) to allow for the large scale production of GHRH-R. There is also a need for a vector, host cell, or host organisms comprising a nucleic acid sequence encoding protein or polypeptides having the activity of GHRH-R.

Large scale production of the cloned chicken GHRH receptor would enable the screening of large numbers of GHRH analogs for identification of improved agonists and antagonists. Such agonists and antagonists will have utility in improving feed utilization and enhancing the efficient production of larger, leaner chickens and other avian species used for meat production.

SUMMARY OF THE INVENTION

The chicken GHRH receptor has been cloned and functions similar to the natural source tissue (chicken pituitary cells) in that it responds to human GHRH but not to the reported chicken hormone. This led us to suspect a problem with the supposed chicken GHRH hormone. The chicken GHRH polypeptide was then recloned from freshly flash frozen chicken hypothalami and sequenced. The nucleic acid sequence of the newly isolated chicken GHRH gene did not agree with the published sequence and the synthesized chicken hormone based on this new sequence was found to be active at the cloned chicken GHRH receptor. The present invention is directed to the use of the new chicken GHRH hormone and its corresponding GHRH receptor to enhance the production of larger, leaner chickens and other avian species used for meat production.

BRIEF DESCRIPTION OF THE DRAWINGS

FIG. 2A shows that the published polypeptide is inactive in stimulating second messenger signaling at the cloned chicken GHRH receptor, while FIG. 2B shows that the cloned chicken GHRH polypeptide reported herein is active.

DETAILED DESCRIPTION OF THE INVENTION

Figure 1A:
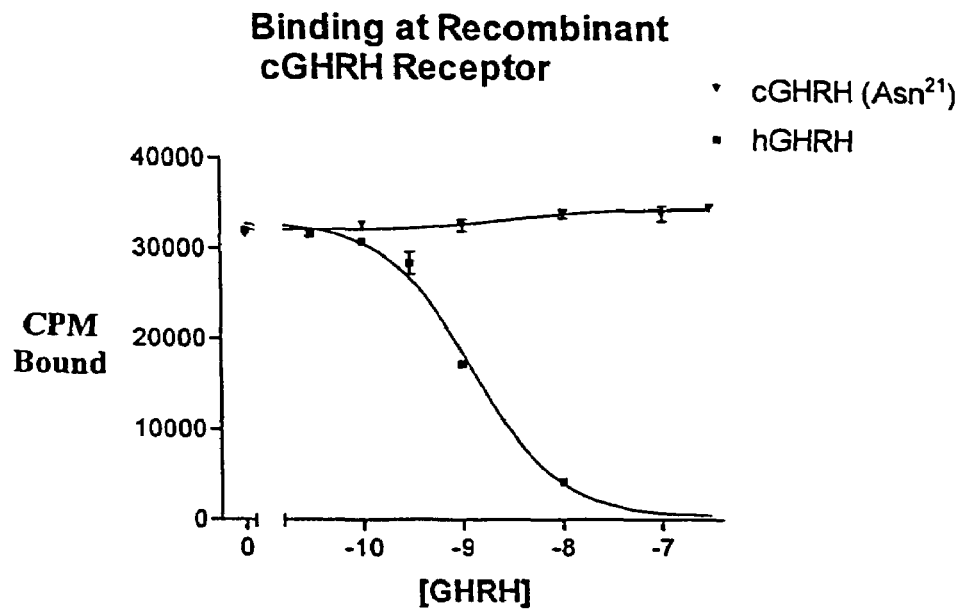
FIGS. 1A and 1B is a graph showing the binding activity of the reported chicken GHRH (FIG. 1A) and the present chicken GHRH (FIG. 1B) at the recombinant chicken GHRH receptor. Binding at recombinant chicken GHRH receptor is competed by the new chicken polypeptide (FIG. 1B) but not by the published polypeptide (FIG. 1A).

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the term "purified" means that the molecule or compound is substantially free of contaminants normally associated with the molecule or compound in a native or natural environment.

The invention also encompasses nucleic acid molecules and polypeptides which differ from actual nucleic acid and polypeptide molecules shown in the Sequence Listing, but which produce the same phenotypic effect. These altered, but phenotypically equivalent nucleic acid and polypeptide molecules are referred to as "equivalent nucleic acids" and "equivalent polypeptides", respectively. This invention also encompasses nucleic acid molecules characterized by changes in non-coding regions that do not alter the phenotype of the polypeptide produced therefrom when compared to the nucleic acid molecule of the present invention. As used herein, the term "nucleic acid" encompasses RNA as well as single and double-stranded DNA and cDNA.

The term "peptide" encompasses a sequence of 3 or more but less than 16 amino acids wherein the amino acids are naturally occurring or synthetic (non-naturally occurring) amino acids. The term polypeptide as used herein is a sequence of 16 or more amino acids wherein the amino acids are naturally occurring or synthetic (non-naturally occurring) amino acids. Peptide or polypeptide mimetics include peptides or polypeptides having one or more of the following modifications:

1. sequences wherein one or more of the peptidyl —C(O)NR— linkages (bonds) have been replaced by a non-peptidyl linkage such as a —$CH_2$ carbamate linkage (—$CH_2$OC(O)NR—), a phosphonate linkage, a —$CH_2$-sulfonamide (—CH $_2$—S(O)$_2$NR—) linkage, a urea (—NHC(O)NH—) linkage, a —$CH_2$-secondary amine linkage, or with an alkylated peptidyl linkage (—C(O)NR—) wherein R is $C_1$–$C_4$ alkyl;

2. sequences wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or $C_1$–$C_4$ alkyl with the proviso that R and R$_1$ are not both hydrogen;

3. sequences wherein the C terminus is derivatized to —C(O)R$_2$ where R$_2$ is selected from the group consisting of $C_1$–$C_4$ alkoxy, and —NR$_3$R$_4$ where R$_3$ and R$_4$ are independently selected from the group consisting of hydrogen and $C_1$–$C_4$ alkyl.

Naturally occurring amino acid residues in peptides/polypeptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Ash or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide/polypeptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-al-pha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" are defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "biologically active fragments" of the GHRH receptor encompasses natural or synthetic portions of the full-length receptor which are capable of binding a receptor-specific ligand (i.e. GHRH polypeptide), or which are capable of eliciting in a host animal GHRH-R specific antisera or a second messenger response while either conjugated to a carrier or in nonconjugated form.

In mammals growth hormone releasing hormone (GHRH) stimulates GH release and synthesis from the somatotropes of the anterior pituitary. The GHRH receptor is a member of family B of the seven transmembrane, G-protein coupled receptors. In the chicken, GHRH polypeptides from mammals and fish stimulate GH release from the pituitary in vivo and in vitro suggesting the presence of GHRH like receptors on the chicken somatotropes, however, the recently cloned and synthesized chicken GHRH is a very poor GH secretagogue. In addition a specific GHRH receptor has not been characterized in the chicken, raising questions about the regulation of GH secretion. A zoo blot probed with a 1 kb fragment of human GHRH receptor DNA failed to elicit a signal in the chicken. This raises questions about the regulation of GH secretion in the chicken.

As described herein the chicken GHRH has now been isolated and used to identify a new chicken GHRH that is capable of activating the chicken GHRH receptor. The identification of the chicken GHRH receptor implies that GH secretion is under the control of regulatory mechanisms similar to those in mammals and will allow more detailed study of this endocrine system in chickens. It will also contribute to structure/function studies of how the GHRH receptor works by indicating receptor domains that are required to be conserved and those that are important for ligand specificity. The chicken GHRH receptor will also be used in accordance with the present invention to identify GHRH analogs and mimetics that stimulate GH release in poultry. This will have great use agriculturally for the improvement of feed utilization and the efficient production of larger, leaner chickens and other commercially viable avian species.

The present invention is directed to the use of the chicken GHRH polypeptide and the chicken GHRH receptor to enhance the production of larger, leaner chickens and other avian species used for meat production and enhance feed utilization. In accordance with one embodiment, a chicken GHRH polypeptide, comprising the amino acid sequence of SEQ ID NO: 1 or a polypeptide that differs from SEQ ID NO: 1 by one or more conservative amino acid substitutions yet retains its ability to stimulate second messenger signaling at the cloned chicken GHRH receptor, is administered to an agriculturally significant avian species to enhance the growth of the avian species.

The sequence of a chicken GHRH polypeptide has been previously reported however that polypeptide has been tested in chickens and chicken pituitary cells, and had little or no GH releasing activity while human GHRH was found to be active. The present invention is directed to GHRH polypeptides that are capable of stimulating second messenger signaling at the chicken GHRH receptor comprising the sequence of SEQ ID NO:4. The nucleotide sequence of the chicken GHRH receptor gene, with the 5' and 3' untranslated region (start codon located at bp 54, stop codon located at bp 1312) is shown as SEQ ID NO: 3. The coding sequence of chicken GHRH receptor is shown as SEQ ID NO: 6. In accordance with one embodiment of the present invention a chicken GHRH having the amino acid sequence of SEQ ID NO: 2 is provided. This sequence differs from the previously reported sequence at amino acid number 21, wherein the present sequence has a lysine and the previously reported sequence has an asparagines.

Synthesis of the chicken GHRH(1–33)NH$_2$, based on the nucleotide sequence of SEQ ID NO: 1, produced a polypeptide that is active in binding to chicken pituitary membranes and competes with human GHRH. At the recombinant chicken GHRH receptor the new polypeptide is active in binding and in signaling through the second messenger cAMP. This new chicken polypeptide is thus a functional GHRH. While the new sequence is active, it is less potent at the chicken receptor than human GHRH. This may be inherent to chicken physiology, or it may be an artifact of the truncated polypeptide (1–33) that was tested. Only amino acids 1–29 are required for full GHRH activity in mammalian systems that have been tested. This may be different in other animals. Active fragments of the chicken GHRH are also within the scope of this invention, including but not limited to truncated polypeptides that include amino acid residues (1–33) and 1–29 of SEQ ID NO: 2, respectively. Thus, one aspect of the present invention relates to a substantially pure protein and biologically active fragments thereof having chicken growth hormone releasing hormone (GHRH) receptor activity.

The present invention also encompasses nucleic acid sequences that encode a peptide or polypeptide that binds to chicken GHRH receptor and is capable of signaling through the second messenger cAMP is provided. In one preferred embodiment the nucleic acid comprises the sequence of SEQ ID NO: 1. In one embodiment a transgenic avian species is provided wherein one or more of the chickens cells comprise a nucleic acid sequence encoding the chicken GHRH protein of SEQ ID NO: 2. Accordingly, the present invention provides for recombinant organisms and progeny thereof comprising an exogenous gene encoding for a chicken GHRH and biologically active fragments thereof.

The present invention is also directed to pharmaceutical formulations comprising the chicken GHRH polypeptide for administration to avian species (preferably to chickens) wherein the GHRH polypeptide interacts with the chicken GHRH receptor and produces a signal through a secondary messenger molecule. The chicken GHRH polypeptide compositions are administered to chickens to enhance feed utilization and enhance the growth and production of lean muscle mass in an avian species. In preferred embodiments the administered GHRH polypeptide comprises the amino acid sequence of SEQ ID NO: 2.

The present invention is also directed to the GHRH receptor (GHRH-R) that binds to the GHRH polypeptide in vivo. The present invention provides the amino acid sequences of chicken GHRH-R and biologically active fragments thereof, as well as oligonucleotide probes or primers which can hybridize to a gene encoding chicken GHRH-R or fragments thereof. In a preferred embodiment, the invention provides for an isolated nucleic acid sequence encoding a GHRH receptor, recombinant vectors including said sequence and host cells containing said sequence useful in production of a GHRH-receptor or biologically active fragments thereof (including proteins and polypeptides having GHRH-R activity).

Preferably, a gene encoding for a protein or polypeptide having chicken GHRH-R activity is isolated and connected with a vector DNA to form a recombinant DNA; the vector DNA including said gene is capable of replicating in a prokaryotic or eukaryotic cell. The gene encoding for a protein or polypeptide having chicken GHRH-R activity is located downstream of a promoter in the vector, and is replicated as part of the vector. The recombinant DNA is then incorporated into a host cell, which did not previously contain said gene, to form a transformed or transected cell line capable of expressing chicken GHRH-R or biologically active fragments thereof. Accordingly, the present invention also provides for recombinant organisms and progeny thereof comprising an exogenous gene encoding for a chicken GHRH-R and biologically active fragments thereof.

The invention is also directed to pharmaceutical compositions comprising an effective amount of the pure receptor or fragments thereof, or proteins and polypeptides having chicken GHRH-R activity in combination with a pharmaceutically acceptable carrier, and provides a method for the therapeutic use of such pharmaceutical compositions. The receptor and receptor fragments (proteins and polypeptides having chicken GHRH-R ligand binding or immunological activity) are useful in screening methods for identifying chicken GHRH analogs, as well as in identifying compounds which may act as chicken GHRH antagonists at the receptor site. In one embodiment GHRH-R is attached to an inert substrate (such as a polymer bead) using standard techniques known to the skilled practitioner. Such bound material can be contacted with a solution of potential GHRH analogs under conditions that allow binding. The material can then be washed to allow for the removal of non-specifically bound compounds, and thus identifying the remaining GHRH analogs.

In accordance with one embodiment of the present invention, a purified nucleic acid sequence is provided that encodes for the chicken growth hormone releasing hormone receptor or biologically active fragments thereof. In yet another embodiment of the present invention a vector comprising a nucleic acid sequence encoding a chicken GHRH polypeptide or chicken GHRH receptor, or biologically active fragments thereof, is provided. In one embodiment the vector is an expression vector that is operably linked to nucleic acid sequences that encode the GHRH polypeptide or the GHRH receptor. Such recombinant expression vectors can be used to transform cells to produce a host cell or living cell line comprising a nucleic acid sequence encoding a growth hormone releasing hormone receptor or biologically active fragment thereof. In accordance with one embodiment a transgenic avian species is produced (preferably a chicken) wherein the avian species comprises one or more cells that express exogenously introduced recombinant GHRH polypeptide or the GHRH receptor.

It is a further object of the present invention to provide a pharmaceutical composition comprising the GHRH polypeptide of SEQ ID NO: 2, or biologically active fragment thereof, and a therapeutic method for administering an effective amount of same to an organism to bind to endogenous GHRH receptor.

There is further a need for screening assays which utilize chicken GHRH-R or biologically active fragments thereof for testing compounds which may interact with chicken GHRH-R or fragments thereof. Preferably such compounds will have physiological properties that allow the compounds to be administered orally. Further, it is another object of the present invention to produce recombinant chicken GHRH-R in sufficient amounts to allow large scale screening of polypeptides and xenobiotics for chicken GHRH-R receptor binding ability.

The isolated chicken GHRH receptor is also useful in raising GHRH-R specific antibodies. Such antibodies may, by blocking the receptor site, effectively prevent GHRH binding and thereby block growth. Other antibodies can be used to activate the GHRH-R receptor (e.g., thyroid stimulating antibodies, such as those causing Graves Disease). Accordingly, the chicken GHRH-R, or an immunogenic portion thereof can be used to elicit antibodies which bind to the receptor and thereby induce or block activity. In accordance with one embodiment, the antigenic peptide fragment of SEQ ID NO: 5 is used to elicit antibody production. Pharmaceutical compositions containing the receptor or segment fragments can be used to treat disorders resulting from or associated with an excess of circulating GHRH. Such compositions can be employed for in vivo administration to bind circulating GHRH, thus preventing its binding to endogenous receptor.

The technique of hydrophilicity analysis of primary sequence information has been commonly used to identify both hydrophobic potentially membrane-spanning domains and hydrophilic antigenic sites. Analysis of the cloned GHRH receptor by the Hopp and Woods Method, see FIG. 18 (Hopp, T. P., and Woods, K. R., Proc. Natl. Acad., 78:3824 (1981) indicates seven domains rich in hydrophobic residues; this is a common property in the G-protein linked receptor family Wang, H., Lipfert, L., Malbon, C., and Bahouth, B., J. Biol. Chem., 264:14424 (1989). This model depicts four extracellular regions which are potential targets for binding of anti-receptor antibodies; three extracellular loops (EC-1, EC-2, EC-3) and an N-terminus which contains sites for asparagine-linked glycosylation.

For purposes of producing antibodies which block or activate the receptor, extracellular loop fragments, particularly those not containing N-glycosylation sites (carbohydrate may sterically interfere with antibody binding) are preferred. However, intracellular loops (IC) are also useful in production of antibodies which may be used for solid phase binding of the receptor protein in screening and other assays. A recent study of antibodies directed against the three EC loops of the thyrotropin receptor indicates a heterogeneity in their biological activities, including the induction of blocking antibodies using the EC-3 Loop as the antigen. See Ohmori, M., et al., Biochem. Biophys. Res. Comm., 174:399 (1991). Therefore, a broad panel of anti-polypeptide and anti-receptor antibodies is prepared and carefully evaluated in order to determine the epitopes required for the induction of blocking or activating antibodies.

To prepare antibodies in accordance with the present invention, polypeptides are produced by conventional solid phase synthesis cleaved by HF, and HPLC purified (van Regenmortal, M. H., In Synthetic Polypeptides as Antigens, Elsevier, New York, pages 41–93 (1988). Polypeptides are then typically coupled to a carrier immunogen such as keyhole limpet haemocyanin (KLH) or ovalbumin via glutaraldehyde by conventional procedures, and these conjugates used to immunize mice and rabbits. See Coligan, J1 et al., In Current Protocols in Immunology, Vol. 1, Wiley-Interscience, New York (1991). Animals are given the first immunization of conjugate polypeptide with Freunds Complete Adjuvant and three weeks later are given weekly booster immunizations with conjugate polypeptide in Freunds incomplete Adjuvant. Specific anti-polypeptide antibodies are detected by their binding to polypeptide in an ELISA or RIA assay. In those instances where polypeptides do not adhere to plastic, and therefore are not amenable for direct assay, then the polypeptide is conjugated to an unrelated carrier protein which then adheres to the plate.

The specificity of the antibodies is also evaluated by the technique of Western Blotting. See Towbin, lt. et al., PNAS USA, 76:4350 (1979). Specific antibodies reorganize a 55 kDa protein in crude membrane preparations, in WGA eluted glycoproteins, or in streptavidin eluates. Membranes from a cell line devoid of receptor serve as a negative control. This procedure also gives information about the degree of cross-reactivity of the antibodies with receptor subtypes from other cell lines and tissues (brain, pituitary) and obviates the need for receptor purification from each source. It is beneficial to obtain both tissue-specific antibodies for physiological studies and cross-reactive antibodies for possible use in purification of the receptor from various tissues using immunoaffinity chromatography.

Monoclonal antibodies to the GHRH receptor are prepared using conventional methods. See Harlow, H., and Lane, D., In Antibodies: A Laboratory Manual, Cold Spring Harbor Lab, New York, pages 139–240 (1988). The antigens used for immunization include (1) KLH-polypeptide conjugates corresponding to the extracellular regions as described above, (2) purified receptor from chicken anterior pituitary membranes, (3) purified receptor deglycosylated with neuraminidase or N-glycosidase and repurified by SDS-PAGE and electro-elution, (4) receptor purified from recombinant sources, such as transected CHO cells, or baculovirus tested for reactivity to the polypeptide immunogen by ELISA or protein immunogen by Western blot. Those which display circulating antibodies to the receptor or its polypeptides are utilized for the preparation of hybridomas. Briefly, spleen cells are removed and fused in the presence of polyethylene glycol to SP2/D myeloma cells that are deficient in the enzyme hypoxanthine-guanine phosphoribosyl aminopterine-thymidine, which selects for true hybrids of both cell types since spleen cells do not grow in culture. Hybridoma supernates are screened for antibody to the receptor by (I) Western blots of purified receptor or WGA-eluted glycoproteins, (2) ELISA using inhibition of radio-labelled ligand binding to membranes. Those hybridomas which are positive are propagated and recloned by limiting dilution or growth in soft agar; this ensures their monoclonal nature. Positive clones are used to induce tumors in mice and accumulate the antibody in ascites fluid.

Both polyclonal and monoclonal IgG antibodies are purified by conventional ammonium sulfate precipitation and Protein A chromatography. See Harlow, supra. Antibodies are analyzed for their ability to block or activate radioligand binding to membranes in the standard binding assay described above.

Those antibodies that show promise for ligand blocking or activation are tested in vivo using for example a rat model, e.g., by using indwelling venous catheters on rats in order to monitor GH levels after administration of anti-GHRH receptor antibody. See Miell, J., et al., J. Endocrinol, 131:75 (1991). Those antibodies which show the most in vivo activity at this point are examined to define their epitopes (if not already determined) on the receptor. Those epitopes represent antigenic fragments of the receptor which when used as immunogens induce antibodies possessing the desired physiological effect of altering levels of GH production.

EXAMPLE 1

Isolation of the Chicken GHRH Polypeptide

RT-PCR with nested PCR primers was used to amplify the full coding region of the chicken GHRH polypeptide. The hypothalami from 10 chickens were snap frozen within two minutes of death and stored at −70° C. RNA was extracted from the hypothalami using TriReagent. The RNA was used in a reverse transcriptase (SuperScript) reaction prior to a polymerase chain reaction (Taq polymerase). The PCR products were purified by agarose gel electrophoresis and a Quiagen affinity column and then cloned into the pTarget vector (Promega) using $T_4$ ligase overnight at 15° C. The ligation reactions used to transform *E. coli* (JM109) were selected and screened by PCR to identify clones containing the GHRH cDNA.

Positive colonies were used to inoculate Luria broth containing ampicillin that was incubated overnight at 37° C. in a shaker. The plasmid DNA was purified from the bacteria using a Quiaprep spin Mini-Prep Kit (Quiagen). A total of nine clones from two different PCR reactions were sequenced (both forward and backward) using an automated ABI dye sequencer, and all showed lysine at position 21. The resultant cDNA sequence is shown in SEQ ID NO: 1, and the encoded polypeptide in SEQ ID NO: 2.

EXAMPLE 2

Isolation of the Chicken GHRH Receptor

The anterior pituitary glands were removed from 100 chicks, snap frozen within two minutes of death and stored at −70 C. RNA was extracted from the pituitaries using TriReagent. The bulk of the RNA was methyl mercury denatured, primed using a combination of random and oligo(dT), and used to create a size selected cDNA library in Lambda Zap II phage.

Figure 3:
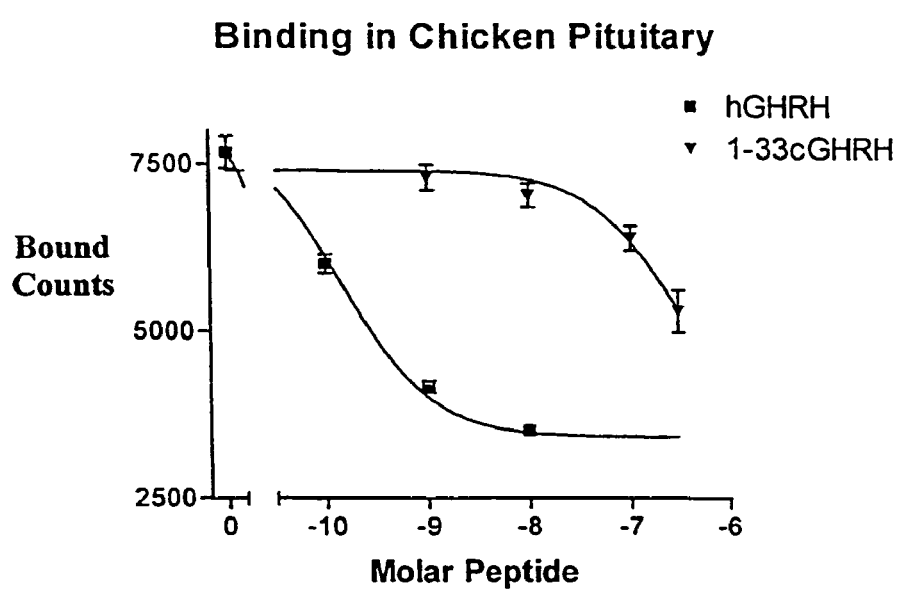
FIG. 3 Binding activity at chicken pituitary membranes, showing that the new polypeptide sequence is active at the endogenous receptor in chicken pituitaries.

The remaining RNA was used to perform RT-PCR reactions utilizing degenerate primers designed to detect all known GHRH receptor cDNAs. A short segment of cDNA was sequenced confirming that we were dealing with the GHRH receptor. Specific primers were designed from this sequence which were used to screen the cDNA library for a full length receptor cDNA clone. The resultant cDNA sequence for the GHRH receptor is shown in SEQ ID NO: 3, and the encoded polypeptide in SEQ ID NO: 4. (FIGS. 3 & 4). The chicken cDNA sequence has less than 63% identity with the human GHRH receptor compared to 83 to 96% identity among known mammalian GHRH receptors.

EXAMPLE 3

Competitive Binding Experiments with Chicken GHRH Receptor

Figure 1B:
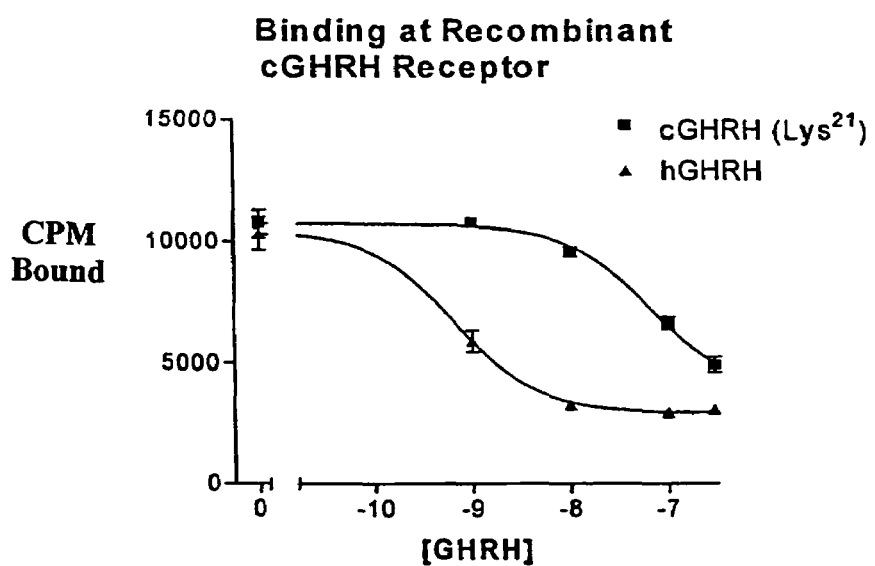

Labeled human GHRH (hGHRH) was bound to recombinant chicken GHRH receptor and the labeled GHRH was competed off with non-labeled chicken or human GHRH. FIGS. 1A and 1B present the data from a competition experiment. The data show chicken GHRH polypeptide (asparagine$^{21}$) [(cGHRH(Asp$^{21}$)] failed to compete with hGHRH (FIG. 1A) whereas chicken GHRH polypeptide (lysine$^{21}$) [(cGHRH(Ly$^{21}$)] did compete with hGHRH (FIG. 1B) for binding to the cGHRH receptor.

In addition, a competition experiment utilizing chicken pituitary membranes (that express the natural GHRH receptors) demonstrated that (cGHRH(Lys$^{21}$) bound with high affinity (i.e. by competing with bound labeled hGHRH) to the receptors, whereas the reported (asparagine$^{21}$) chicken GHRH did not. The previously reported chicken GHRH polypeptide also had no activity in binding or signaling at the cloned recombinant chicken GHRH receptor.

Figure 2A:
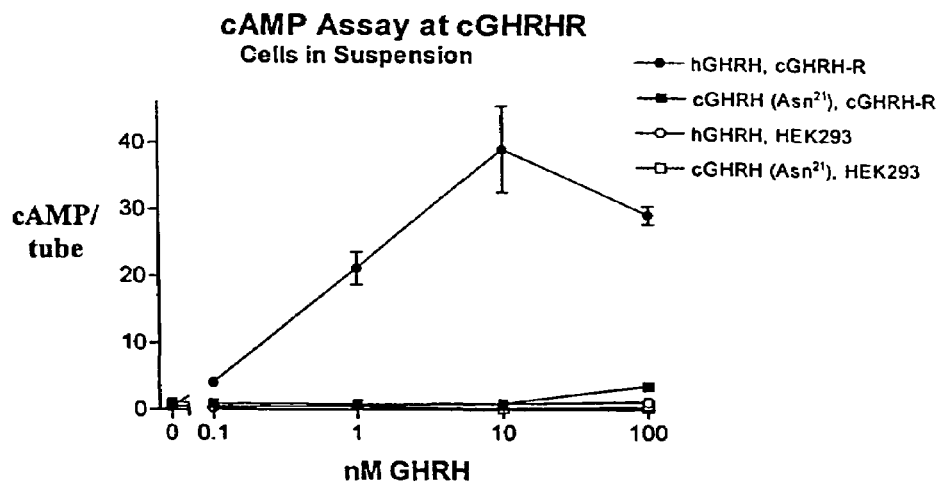
FIGS. 2A and 2B is a graph showing cAMP signaling through the recombinant chicken GHRH receptor.
Figure 2B:
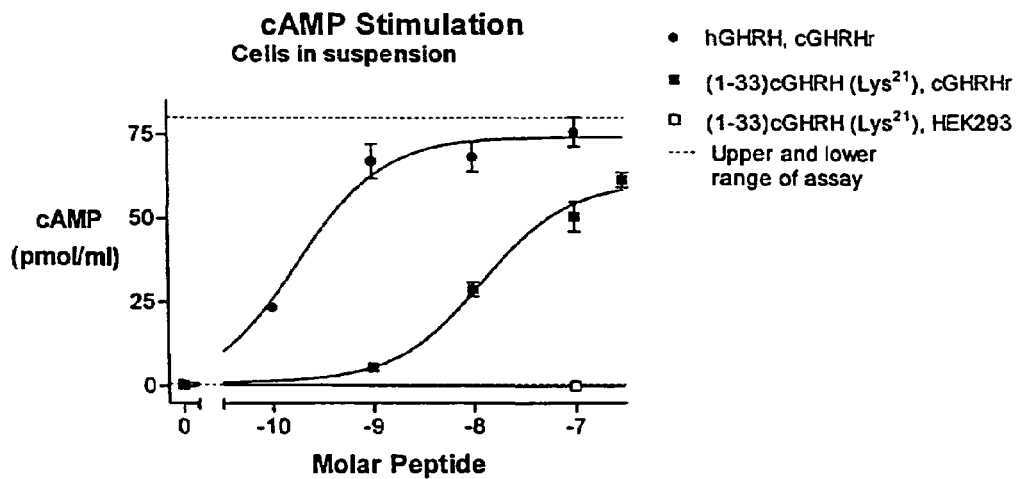

FIGS. 2A and 2B show the results of GHRH mediated cAMP stimulation in HEK293 cells expressing the cGHRH receptor. Cells lacking the cGHRH receptor (HEK293) were used as the control. The data show cGHRH(Asp$^{21}$) is inactive in stimulating second messenger signaling at the cloned chicken GHRH receptor (FIG. 2A), while FIG. 2B shows that (cGHRH(Lys$^{21}$) is active.

EXAMPLE 4

Therapeutic Utility of the GHRH-R

The chicken GHRH-R can be used to increase growth in domestic livestock, as well as improve immune functions, appetite control, feed efficiency and nutrition. We have used RT-PCR with degenerate primers to amplify fragments of GHRH receptor cDNA from RNA prepared from flash frozen chicken pituitaries. These fragments were then sequenced and used to identify a full length chicken receptor cDNA clone from a chicken pituitary cDNA library. Initial attempts using an available chicken pituitary cDNA library failed because the abundance of receptor message was too low. The available chicken pituitary libraries did not have sufficient complexity to include such rare messages.

In one embodiment, the chicken (*Gallus gallus*) GHRH receptor sequence is used to map the binding site of GHRH on its receptor. Mapping of the site is conducted using a series of photoaffinity crosslinking probes followed by analysis of protease cleavage maps. The differences between different species allows the identification of functional sites within receptor domains. Characterizing the binding site will lead to the development of GHRH analogs and mimetics that provide pharmacological means to alter GH release.

The chicken GHRH receptor will also be used to identify GHRH analogs and mimetics that stimulate GH release in poultry. In accordance with one embodiment the nucleic acid sequence of SEQ ID NO: 3 or SEQ ID NO: 6 is used as a probe to isolate related genes from chicken and other avian species. This could be important agriculturally for the improvement of feed utilization and the efficient production of larger, leaner chickens and other avian species used for meat production.

The invention claimed is:
1. A purified nucleic acid sequence encoding the chicken GHRH receptor, said sequence comprising the nucleic acid sequence of SEQ ID NO: 3.

* * * * *

SEQUENCE LISTING

<160> NUMBER OF SEQ ID NOS: 6

<210> SEQ ID NO 1
<211> LENGTH: 138
<212> TYPE: DNA
<213> ORGANISM: Gallus gallus

<400> SEQUENCE: 1
cacgccgatg ggatcttcag caaagcctac aggaaactcc tgggccagct gtccgcaagg     60
aaatacctgc actccctgat ggccaagcgg gtcggcggtg ccagcagcgg cctgggggac    120
gaggcggaac cgctcagc                                                  138

<210> SEQ ID NO 2
<211> LENGTH: 46
<212> TYPE: PRT
<213> ORGANISM: Gallus gallus

<400> SEQUENCE: 2

His Ala Asp Gly Ile Phe Ser Lys Ala Tyr Arg Lys Leu Leu Gly Gln
 1               5                  10                  15

Leu Ser Ala Arg Lys Tyr Leu His Ser Leu Met Ala Lys Arg Val Gly
            20                  25                  30

Gly Ala Ser Ser Gly Leu Gly Asp Glu Ala Glu Pro Leu Ser
        35                  40                  45

<210> SEQ ID NO 3
<211> LENGTH: 1689
<212> TYPE: DNA
<213> ORGANISM: Gallus gallus

<400> SEQUENCE: 3
taaggaagat aaaagaatta aagtctgact ttgctttgga acacgaatcc tagcatgtca     60
taccactgtg tcctgtacac actgactctt gcggtgcttg ttgctgggaa tgtccatccg    120
gaatgtgatt ttatagcaga gctgaagaaa aaggaggctg aatgcctgga gaactcagag    180
gagcatgaga atgcaacatc aggttgcaag aaaacctggg acaaattact ctgctggcca    240
gaggcagatg ctggagagac tcttgcctta ccttgcccag acatcctctt tcacttcatg    300
gaagaaccag ctgggatagt aagaagaaac tgcacaaaga aggctggtc agagccattc     360 ccttcctatc acattgcttg tccagttgaa gatgagattc cacttgaaga caatcctac    420 ttttctacga taaagatcat atataccgta ggatacagtt tgtctattac ctcactcatt    480
attgctgtga cagttcttat ggcattcagg aggctacgct gccccagaaa ttacatccac    540
atacagctct tttttacttt catcttaaag gctattgcca ttttcataaa ggattctgtc    600
cttttccaag aggaagacat tgaccattgc agctttttcta caactgaatg caagatctca    660
gttgttttct gtcactactt catgatgacc aatttcatat ggctgctggt agaggcccttt    720 taccttaact gtctactact ctcatccctt tctcatggaa aagatatttt ctggtggctg    780
gttctctttg ctggggttt tccaacactt ttcacctta tatgggtatt agcaaaattc    840
tactttgaag acacagcatg ctgggatatt aatcaagact ctccttactg gtggctaatc    900
aaagggccta ttgtaatttc tgttggggtc aattttgtct tatttatcaa catcatcaga    960
attttgctga aaaactaga tcctagacaa atcaacttca ataactcatc tcagtacaga   1020
cgcctctcaa ggtcaactct gcttctaatt ccattatttg gaacccatta tattgtcttc   1080

-continued

```
aacttccttc cggaatatac cagccttggc attcggcttt atttagagct ctgcattgga    1140
tcttttcagg ggtttattgt agcactcctc tactgtttcc tgaaccaaga ggtgcaaacg    1200
gaaataggtc ggagatggca cggtaagaga tatggactta tgccagtttg gagaaggaca    1260
agatggactg tgccaaccag ttctggagta aaaatgaata catctgtgtg ctaaagacaa    1320
cctccgaatc tggagtaatc acaataataa gcctggttag ggaaaacaaa caacaacaga    1380
aaatccttaa caatgacagt ttactgagag caaattggag gaaaatttct gcagaaattc    1440
tgcccaccag ctatctcttg ctttacaagt gctgaagtga tggattgact gactgtccga    1500
ttaaaatcgc cctttcatgg gctattacaa cacagcaaat gcagatattg cctctttttc    1560
attccctgtc catactctct tactaatgaa ctgtatagca taatgtgtca gggagtgggc    1620
accaggagca cccttcagtg acaccataga tcgccagctc tggaaatgaa tactcagtct    1680
tcacacaga                                                            1689
```

<210> SEQ ID NO 4
<211> LENGTH: 419
<212> TYPE: PRT
<213> ORGANISM: Gallus gallus

<400> SEQUENCE: 4

```
Met Ser Tyr His Cys Val Leu Tyr Thr Leu Thr Leu Ala Val Leu Val
 1               5                  10                  15

Ala Gly Asn Val His Pro Glu Cys Asp Phe Ile Ala Glu Leu Lys Lys
            20                  25                  30

Lys Glu Ala Glu Cys Leu Glu Asn Ser Glu Glu His Glu Asn Ala Thr
        35                  40                  45

Ser Gly Cys Lys Lys Thr Trp Asp Lys Leu Leu Cys Trp Pro Glu Ala
    50                  55                  60

Asp Ala Gly Glu Thr Leu Ala Leu Pro Cys Pro Asp Ile Leu Phe His
65                  70                  75                  80

Phe Met Glu Glu Pro Ala Gly Ile Val Arg Arg Asn Cys Thr Lys Lys
                85                  90                  95

Gly Trp Ser Glu Pro Phe Pro Ser Tyr His Ile Ala Cys Pro Val Glu
            100                 105                 110

Asp Glu Ile Pro Leu Glu Glu Gln Ser Tyr Phe Ser Thr Ile Lys Ile
        115                 120                 125

Ile Tyr Thr Val Gly Tyr Ser Leu Ser Ile Thr Ser Leu Ile Ile Ala
    130                 135                 140

Val Thr Val Leu Met Ala Phe Arg Arg Leu Arg Cys Pro Arg Asn Tyr
145                 150                 155                 160

Ile His Ile Gln Leu Phe Phe Thr Phe Ile Leu Lys Ala Ile Ala Ile
                165                 170                 175

Phe Ile Lys Asp Ser Val Leu Phe Gln Glu Glu Asp Ile Asp His Cys
            180                 185                 190

Ser Phe Ser Thr Thr Glu Cys Lys Ile Ser Val Val Phe Cys His Tyr
        195                 200                 205

Phe Met Met Thr Asn Phe Ile Trp Leu Leu Val Glu Ala Leu Tyr Leu
    210                 215                 220

Asn Cys Leu Leu Leu Ser Ser Leu Ser His Gly Arg Arg Tyr Phe Trp
225                 230                 235                 240

Trp Leu Val Leu Phe Gly Trp Gly Phe Pro Thr Leu Phe Thr Phe Ile
                245                 250                 255

Trp Val Leu Ala Lys Phe Tyr Phe Glu Asp Thr Ala Cys Trp Asp Ile
```

```
                    260              265              270
Asn Gln Asp Ser Pro Tyr Trp Trp Leu Ile Lys Gly Pro Ile Val Ile
            275              280              285
Ser Val Gly Val Asn Phe Val Leu Phe Ile Asn Ile Ile Arg Ile Leu
        290              295              300
Leu Lys Lys Leu Asp Pro Arg Gln Ile Asn Phe Asn Asn Ser Ser Gln
305              310              315              320
Tyr Arg Arg Leu Ser Arg Ser Thr Leu Leu Leu Ile Pro Leu Phe Gly
                325              330              335
Thr His Tyr Ile Val Phe Asn Phe Leu Pro Glu Tyr Thr Ser Leu Gly
            340              345              350
Ile Arg Leu Tyr Leu Glu Leu Cys Ile Gly Ser Phe Gln Gly Phe Ile
        355              360              365
Val Ala Leu Leu Tyr Cys Phe Leu Asn Gln Glu Val Gln Thr Glu Ile
    370              375              380
Gly Arg Arg Trp His Gly Lys Arg Tyr Gly Leu Met Pro Val Trp Arg
385              390              395              400
Arg Thr Arg Trp Thr Val Pro Thr Ser Ser Gly Val Lys Met Asn Thr
                405              410              415
Ser Val Cys

<210> SEQ ID NO 5
<211> LENGTH: 23
<212> TYPE: PRT
<213> ORGANISM: Gallus gallus

<400> SEQUENCE: 5

Ser Lys Ala Tyr Arg Lys Leu Leu Gly Gln Leu Ser Ala Arg Leu Tyr
1               5                   10                  15

Leu His Ser Leu Met Ala Lys
            20

<210> SEQ ID NO 6
<211> LENGTH: 1260
<212> TYPE: DNA
<213> ORGANISM: Gallus gallus

<400> SEQUENCE: 6
atgtcatacc actgtgtcct gtacacactg actcttgcgg tgcttgttgc tgggaatgtc      60
catccggaat gtgattttat agcagagctg aagaaaaagg aggctgaatg cctggagaac     120
tcagaggagc atgagaatgc aacatcaggt tgcaagaaaa cctgggacaa attactctgc     180
tggccagagg cagatgctgg agagactctt gccttacctt gcccagacat cctctttcac     240
ttcatggaag aaccagctgg gatagtaaga agaaactgca caaagaaagg ctggtcagag     300
ccattccctt cctatcacat tgcttgtcca gttgaagatg agattccact tgaagaacaa     360
tcctactttt ctacgataaa gatcatatat accgtaggat acagtttgtc tattacctca     420
ctcattattg ctgtgacagt tcttatggca ttcaggaggc tacgctgccc cagaaattac     480
atccacatac agctcttttt tactttcatc ttaaaggcta ttgccatttt cataaaggat     540
tctgtccttt tccaagagga agacattgac cattgcagct tttctacaac tgaatgcaag     600
atctcagttg ttttctgtca ctacttcatg atgaccaatt tcatatggct gctggtagag     660 gcccttacc ttaactgtct actactctca tcccttttctc atggaagaag atatttctgg     720
tggctggttc tctttggctg gggttttcca acacttttca cctttatatg ggtattagca     780
```

-continued

| | | | | | |
|---|---|---|---|---|---|
| aaattctact | ttgaagacac | agcatgctgg | gatattaatc | aagactctcc | ttactggtgg | 840 |
| ctaatcaaag | ggcctattgt | aatttctgtt | ggggtcaatt | ttgtcttatt | tatcaacatc | 900 |
| atcagaattt | tgctgaaaaa | actagatcct | agacaaatca | acttcaataa | ctcatctcag | 960 |
| tacagacgcc | tctcaaggtc | aactctgctt | ctaattccat | tatttggaac | ccattatatt | 1020 |
| gtcttcaact | tccttccgga | ataccagc | cttggcattc | ggctttattt | agagctctgc | 1080 |
| attggatctt | ttcaggggtt | tattgtagca | ctcctctact | gtttcctgaa | ccaagaggtg | 1140 |
| caaacggaaa | taggtcggag | atggcacggt | aagagatatg | gacttatgcc | agtttggaga | 1200 |
| aggacaagat | ggactgtgcc | aaccagttct | ggagtaaaaa | tgaatacatc | tgtgtgctaa | 1260 |